United States Patent [19]

Berg

[11] Patent Number: 5,118,392
[45] Date of Patent: Jun. 2, 1992

[54] SEPARATION OF TRICHLOROETHYLENE FROM A BUTYL ALCOHOL BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 735,803

[22] Filed: Jul. 25, 1991

[51] Int. Cl.⁵ .......................... B01D 3/40; C07C 17/38; C07C 29/84
[52] U.S. Cl. .................................. 203/57; 203/58; 203/60; 203/62; 203/63; 203/65; 568/913; 570/262
[58] Field of Search .................. 203/63, 58, 65, 62, 203/60, 57; 570/262; 568/913, 918

[56] References Cited

U.S. PATENT DOCUMENTS

| | | | |
|---|---|---|---|
| 3,697,388 | 10/1972 | Hobson et al. | 570/262 |
| 4,036,703 | 7/1977 | Leroi et al. | 203/60 |
| 4,121,978 | 10/1978 | Becuwe | 203/58 |

FOREIGN PATENT DOCUMENTS 418463 8/1974 U.S.S.R. ............................... 203/59

*Primary Examiner*—Wilbur Bascomb, Jr.

[57] ABSTRACT

Trichloroethylene cannot be completely separated from n-butanol, isobutanol, 2-butanol or t-butanol by conventional distillation or rectification because of the minimum boiling azeotropes. Trichloroethylene can be readily separated from n-butanol, isobutanol, 2-butanol or t-butanol by extractive distillation. Typical effective agents are: for n-butanol, dimethylsulfoxide; for isobutanol, n-octanol; for 2-butanol, 2-methyl-1-pentanol and for t-butanol, n-butyl acetate.

4 Claims, No Drawings

SEPARATION OF TRICHLOROETHYLENE FROM A BUTYL ALCOHOL BY EXTRACTIVE DISTILLATION

FIELD OF THE INVENTION

This invention relates to a method for separating trichloroethylene from the butyl alcohols using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component. At the bottom of a continuous column, the less volatile components of the close boiling mixtures and the extractive agent are continuously removed from the column. The usual methods of separation of these two components are the use of another rectification column, cooling and phase separation, or solvent extraction.

Trichloroethylene, B.P.=87° C. forms minimum boiling azeotropes with the four butyl alcohols. With n-butanol, the azeotrope boils at 86.6° C. and contains 97 weight percent trichloroethylene; with isobutanol the azeotrope boils at 85.4° C. and contains 91% trichloroethylene; with 2-butanol the azeotrope boils at 84.2° C. and contains 85% trichloroethylene and with t-butanol the azeotrope boils at 82.6° C. and contains 67% trichloroethylene. Extractive distillation would be an attractive method of effecting the separation of trichloroethylene from these alcohols if agents can be found that (1) will enhance the relative volatility between trichloroethylene and these alcohols and (2) are easy to recover, that is, form no azeotrope with trichloroethylene, n-butanol, isobutanol, 2-butanol or t-butanol and boil sufficiently above these five compounds to make separation by rectification possible with only a few theoretical plates.

Extractive distillation typically requires the addition of an equal amount to twice as much extractive agent as the trichloroethylene-butanol on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the trichloroethylene and alcohols otherwise it will form a two phase azeotrope with it and some other method of separation will have to be employed.

TABLE 1

Effect of Relative Volatility on the Separation of Trichloroethylene From Butanols at 99% Purity.

| Relative Volatility | Theoretical Plates | Actual Plates, 75% Efficiency | Actual Plates, 75% Eff., Min. Reflux |
| --- | --- | --- | --- |
| 1.2 | 50 | 67 | 87 |
| 1.3 | 35 | 47 | 61 |
| 1.4 | 27 | 36 | 47 |
| 1.5 | 23 | 31 | 40 |
| 1.6 | 20 | 27 | 35 |
| 1.7 | 17 | 23 | 29 |

The advantage of employing an effective extractive distillation agent is shown in Table 1. Trichloroethylene forms minimum boiling azeotropes with the butyl alcohols which possess a relative volatility of 1.0 and cannot be separated by rectification. If extractive distillation is employed with an agent yielding a relative volatility of 1.7 or higher, a rectification column of only 29 actual plates will be required.

OBJECTIVE OF THE INVENTION

The objects of this invention are to provide a process or method of extractive distillation that will enhance the relative volatility of trichloroethylene to n-butanol, isobutanol, 2-butanol and t-butanol in their separation in a rectification column. It is a further object of this invention to identify organic compounds that are stable, can be separated from the trichloroethylene or the alcohols by rectification with relatively few plates and can be recycled to the extractive distillation column with little decomposition.

SUMMARY OF THE INVENTION

The objects of this invention are provided by a process for the separation of trichloroethylene from n-butanol, isobutanol, 2-butanol or t-butanol which entails the use of certain organic compounds as the agent in extractive distillation.

DETAILED DESCRIPTION OF THE INVENTION

I have discovered that certain organic compounds will effectively increase the relative volatility between trichloroethylene and n-butanol, isobutanol, 2-butanol or t-butanol by rectification when employed as the agent in extractive distillation. Table 2 lists the compounds that I have found to be effective extractive distillation agents to recover trichloroethylene from n-butanol. The data in Tables 2, 3, 5, 7, 8, 10 and 11 was obtained in a vapor-liquid equilibrium still. In every case, the starting mixture was the trichloroethylene-butanol azeotrope. The relative volatilities are listed for each of the agents. The compounds which are effective extractive distillation agents to remove trichloroethylene from n-butanol are n-decanol, n-nonyl alcohol, n-octanol, n-hexyl alcohol, isodecyl alcohol, tetrahydrofurfuryl alcohol, diisobutyl carbinol, methyl amyl alcohol, cyclohexanol, phenethyl alcohol, benzyl alcohol, 2-methyl pentanol, methyl isobutyl carbinol, isophorone, 5-methyl-2-hexanone, diisobutyl ketone, 2-heptanone, 3-octanone, 2,6-dimethyl-4-heptanone, acetonylacetone, 2-octanone, ethyl valerate, ethyl isovalerate, isobutyl isobutyrate, isobornyl acetate, 1-methoxy-2-propanol acetate, dimethylsulfoxide, dimethylformamide, dimethylacetamide, acetophenone and sulfolane.

Table 3 lists the agents that were found to be ineffective agents for separating trichloroethylene from n-butanol.

One of the agents, dimethylsulfoxide, whose relative volatility had been determined in the vapor-liquid equilibrium still, was then evaluated in a glass perforated plate rectification column possessing 7.3 theoretical plates and the results listed in Table 4. Dimethylsulfoxide gave a relative volatility of 1.28 after two hours of operation.

Table 5 lists the compounds that were found to be effective extractive distillation agents to recover trichloroethylene from isobutanol. The effective agents are benzyl alcohol, 2-methyl-1-pentanol, isohexyl alcohol, 4-methyl-2-pentanol, tetrahydrofurfuryl alcohol, cyclohexanol, n-octanol, 2-octanol, isooctanol, 2-ethyl-1-hexanol, diisobutyl carbinol, heptyl alcohol, phenethyl alcohol, diacetone alcohol, isoamyl alcohol, nonyl alcohol, n-decanol and isophorone.

Table 6 lists the agents that were found to be ineffective agents for separating trichloroethylene from isobutanol.

TABLE 2

Effective Agents For Separating Trichloroethylene From n-Butanol

| Compounds | Relative Volatility |
|---|---|
| n-Decanol | 2.4 |
| n-Nonyl alcohol | 2.5 |
| n-Octanol | 2.3 |
| n-Hexyl alcohol | 3.1 |
| Tetrahydro furfuryl alcohol | 2.2 |
| Isodecyl alcohol | 3.6 |
| Diisobutyl carbinol | 1.4 |
| Methyl amyl alcohol | 1.7 |
| Cyclohexanol | 3.5 |
| Phenethyl alcohol | 2.5 |
| Benzyl alcohol | 3.5 |
| 2-Methyl pentanol | 3.5 |
| Methyl isobutyl carbinol | 2.4 |
| Isophorone | 1.45 |
| 5-Methyl-2-hexanone | 1.6 |
| Diisobutyl ketone | 1.4 |
| 2-Heptanone | 1.7 |
| 3-Octanone | 1.35 |
| 2,6-Dimethyl-4-heptanone | 1.35 |
| Acetonylacetone | 2.6 |
| 2-Octanone | 1.4 |
| Ethyl valerate | 3.0 |
| Ethyl isovalerate | 1.45 |
| Isobutyl isobutyrate | 1.5 |
| Isobornyl acetate | 1.25 |
| 1-Methyoxy-2-propanol acetate | 1.5 |
| Dimethylsulfoxide | 1.3 |
| Dimethylformamide | 4.5 |
| Dimethylacetamide | 4.0 |
| Acetophenone | 1.6 |
| Sulfolane | 2.5 |

TABLE 3

Ineffective Agents, Trichloroethylene-n-Butanol

| 3-Hexanone | Isobutyl heptyl ketone |
|---|---|
| Isobutyl butyrate | Ethyl phenyl acetate |
| Nitromethane | Nitroethane |

TABLE 4

Data From Run Made In Rectification Column

| Agent | Column | Weight % C₂H Cl₃ | Weight % n-Butanol | Time hrs. | Relative Volatility |
|---|---|---|---|---|---|
| Dimethyl-sulfoxide | Overhead | 96.9 | 3.1 | 1 | 1.22 |
| | Bottoms | 88.2 | 11.8 | | |
| Dimethyl-sulfoxide | Overhead | 98.2 | 1.8 | 2 | 1.28 |
| | Bottoms | 90.1 | 9.9 | | |

One of the agents, n-octanol, whose relative volatility had been determined in the vapor-liquid equilibrium still, was then evaluated in the glass perforated plate rectification column and the results listed in Table 6. n-Octanol gave a relative volatility of 1.31 after two hours of operation. Table 7 lists the compounds found to be effective extractive distillation agents to recover trichloroethylene from 2-butanol. The effective agents are isoamyl alcohol, hexyl alcohol, diacetone alcohol, 2-ethyl butanol, 4-methyl-2-pentanol, diisobutyl carbinol, benzyl alcohol, 1-octanol, tetrahydrofurfuryl alcohol, 3-methyl-1-butanol, 2-methyl-1-pentanol, 3-phenyl-1-propanol, isooctyl alcohol, 3-methyl-3-pentanol, heptyl alcohol, cyclohexanol, 2-ethyl-1-hexanol and isononyl alcohol.

Table 8 lists the agents that were found to be ineffective agents for separating trichloroethylene from 2-butanol.

One of the agents, 2-methyl-1-pentanol, whose relative volatility had been determined in the vapor-liquid equilibrium still, was then evaluated in the glass perforated plate rectification column and the results listed in Table 9. 2-Methyl-1-pentanol gave a relative volatility of 1.59 after two hours of operation.

Table 10 lists the compounds found to be effective extractive distillation agents to recover trichloroethylene from t-butanol. The effective agents are n-butyl acetate, n-amyl acetate, n-propyl acetate, isobutyl acetate, hexyl acetate, 2-pentanone, 3-pentanone, 5-methyl-2-hexanone, methyl isobutyl ketone, methyl isopropyl ketone, 3-heptanone, methyl isoamyl ketone, 2-methoxyethyl ether acetate, 1-methoxy-2-propanol acetate, 3-hexanone, diisobutyl ketone, 4-methyl-2-pentanone, ethyl propionate, isoamyl acetate, ethyl isovalerate, ethyl butyrate, 1-methoxy-2-propanol, ethyl valerate, 3-ethoxy propionate, 2,4-pentanedione, isobutyl butyrate, ethyl ethoxy propionate and isobutyl isobutyrate.

Table 11 lists the compounds that were found to be ineffective agents for separating trichloroethylene from t-butanol.

One of the agents, n-butyl acetate, whose relative volatility had been determined in the vapor-liquid equilibrium still, was then evaluated in the glass perforated plate rectification column and the results listed in Table 12. n-Butyl acetate gave a relative volatility of 2.15 after two hours of operation

TABLE 5

Effective Agents For Separating Trichloroethylenene From Isobutanol

| Compounds | Relative Volatility |
|---|---|
| Benzyl alcohol | 2.0 |
| 2-Methyl-1-pentanol | 2.2 |
| Isohexyl alcohol | 2.6 |
| 4-Methyl-2-pentanol | 2.7 |
| Tetrahydrofurfuryl alcohol | 2.4 |
| Cyclohexanol | 2.4 |
| n-Octanol | 1.3 |
| 2-Octanol | 2.7 |
| Isooctanol | 1.6 |
| 2-Ethyl-1-hexanol | 1.8 |
| Diisobutyl carbinol | 1.6 |
| Heptyl alcohol | 1.95 |
| Phenethyl alcohol | 1.55 |
| Diacetone alcohol | 1.3 |
| Isoamyl alcohol | 1.9 |
| Nonyl alcohol | 3.8 |
| n-Decanol | 3.9 |
| Isophorone | 1.6 |

TABLE 6

Data From Run Made In Rectification Column

| Agent | Column | Time hrs. | Weight % $C_2HCl_3$ | Weight % Isobutanol | Relative Volatility |
|---|---|---|---|---|---|
| n-Octanol | Overhead | 1 | 96.9 | 3.1 | 1.275 |
|  | Bottoms |  | 84.0 | 16.0 |  |
| " | Overhead | 2 | 97.7 | 2.3 | 1.31 |
|  | Bottoms |  | 84.8 | 15.2 |  |

THE USEFULNESS OF THE INVENTION

The usefulness or utility of this invention can be demonstrated by referring to the data presented in Tables 2 to 12. All of the successful agents show that trichloroethylene can be separated from n-butanol, isobutanol, 2-butanol or t-butanol by means of extractive distillation in a rectification column and that the ease of separation as measured by relative volatility is considerable.

TABLE 7

Effective Agents For Separating Trichloroethylene From 2-Butanol

| Compounds | Relative Volatility |
|---|---|
| Isoamyl alcohol | 2.4 |
| Hexyl alcohol | 2.6 |
| Diacetone alcohol | 1.45 |
| 2-Ethyl butanol | 1.85 |
| 4-Methyl-2-pentanol | 1.75 |
| Diisobutyl carbinol | 1.35 |
| Benzyl alcohol | 1.8 |
| Tetrahydrofurfuryl alcohol | 1.65 |
| 3-Methyl-1-butanol | 2.5 |
| 2-Methyl-1-pentanol | 1.6 |
| 1-Octanol | 1.5 |
| 3-Phenyl-1-propanol | 1.65 |
| Isooctyl alcohol | 1.7 |
| 3-Methyl-3-pentanol | 1.35 |
| Heptyl alcohol | 1.55 |
| Cyclohexanol | 1.8 |
| 2-Ethyl-1-hexanol | 1.55 |
| Isononyl alcohol | 1.35 |

TABLE 8

Ineffective Agents, Trichloroethylene-2-Butanol

| n-Butyl acetate | n-Propyl acetate |
| n-Amyl acetate | 3-Methoxy-2-propanol acetate |
| 4-Methyl-2-pentanone | Ethyl isovalerate |

TABLE 8-continued

Ineffective Agents, Trichloroethylene-2-Butanol

| 5-Methyl-2-hexanone | Methyl isobutyl ketone |
| 2-Methoxy-2-propanol | Mesityl oxide |

TABLE 9

Data From Run Made In Rectification Column

| Agent | Column | Weight % $C_2HCl_3$ | Weight % 2-Butanol | Relative Volatility | Time hrs. |
|---|---|---|---|---|---|
| 2-Methyl-1-pentanol | Overhead | 97.6 | 2.4 | 1.49 | 1 |
|  | Bottoms | 69.3 | 30.7 |  |  |
| 2-Methyl-1-pentanol | Overhead | 98.2 | 1.8 | 1.59 | 2 |
|  | Bottoms | 65.6 | 34.4 |  |  |

TABLE 10

Effective Agents For Separating Trichloroethylene From t-Butanol

| Compounds | Relative Volatility |
|---|---|
| n-Butyl acetate | 1.7 |
| n-Amyl acetate | 1.7 |
| n-Propyl acetate | 2.9 |
| Isobutyl acetate | 1.4 |
| Hexyl acetate | 1.4 |
| 2-Pentanone | 1.9 |
| 3-Pentanone | 1.45 |
| 5-Methyl-2-hexanone | 1.3 |
| Methyl isobutyl ketone | 1.3 |
| Methyl isopropyl ketone | 1.3 |
| 3-Heptanone | 1.35 |
| Methyl isoamyl ketone | 1.4 |
| 2-Methoxyethyl ether acetate | 1.85 |
| 1-Methoxy-2-propanol acetate | 1.65 |
| 3-Hexanone | 1.55 |
| Diisobutyl ketone | 1.4 |
| 4-Methyl-2-pentanone | 1.5 |
| Ethyl propionate | 2.4 |
| Isoamyl acetate | 1.5 |
| Ethyl isovalerate | 1.5 |
| Ethyl butyrate | 1.5 |
| 1-Methoxy-2-propanol | 1.65 |
| Ethyl valerate | 1.65 |
| 3-Ethoxy propionate | 1.5 |
| 2,4-Pentanedione | 1.4 |
| Isobutyl butyrate | 1.65 |
| Ethyl ethoxy propionate | 1.45 |
| Isobutyl isobutyrate | 1.45 |

TABLE 11

Ineffective Agents, Trichloroethylene-t-Butanol

| Dioxane | 3,3-Dimethyl-2-butanone |
| Dimethyl carbonate | Ethylene glycol ethyl ether acetate |
| Pyridine | Dipropylene glycol methyl ether acetate |
| Ethylene glycol hexyl ether | Dipropylene glycol methyl ether |
| 2-Methoxyethyl ether | Diethylene glycol ethyl ether |

TABLE 12

Data From Run Made In Rectification Column

| Agent | Column | Time hrs. | Weight % $C_2HCl_3$ | Weight % t-Butanol | Relative Volatility |
|---|---|---|---|---|---|
| n-Butyl acetate | Overhead | 1 | 70.3 | 29.7 | 1.63 |
|  | Bottoms |  | 6.1 | 93.9 |  |
| n-Butyl acetate | Overhead | 2 | 92.2 | 7.8 | 2.15 |
|  | Bottoms |  | 4.1 | 95.9 |  |

WORKING EXAMPLES

EXAMPLE 1

Sixty grams of the trichloroethylene-n-butanol azeotrope and 30 grams of dimethylsulfoxide were charged to a vapor-liquid equilibrium still and refluxed for seven hours. Analysis indicated a vapor composition of 97.7% trichloroethylene, 2.3% n-butanol; a liquid composition of 97.1% trichloroethylene, 2.9% n-butanol which is a relative volatility of 1.25.

EXAMPLE 2

A solution comprising 300 grams of trichloroethylene and 15 grams of n-butanol was placed in the stillpot of a 7.3 theoretical plate glass perforated plate rectification column. When refluxing began, an extractive agent comprising dimethylsulfoxide was pumped into the column at a rate of 15 ml/min. The temperature of the extractive agent as it entered the top of the column was 85° C. After establishing the feed rate of the extractive agent, the heat input to the trichloroethylene-n-butanol in the stillpot was adjusted to give a total reflux rate of 40 ml/min. After two hours operation, overhead and bottoms samples were collected and analysed. The overhead analysis was 98.2% trichloroethylene, 1.8% n-butanol and the bottoms analysis was 90.1% trichloroethylene, 9.9% n-butanol. This gives an average relative volatility of 1.28 for each theoretical plate.

EXAMPLE 3

Seventy grams of the trichloroethylene-isobutanol azeotrope and 30 grams of n-octanol were charged to the vapor-liquid equilibrium still and refluxed for five hours. Analysis indicated a vapor composition of 95.4% trichloroethylene, 4.6% isobutanol; a liquid composition of 93.9% trichloroethylene, 6.1% isobutanol which is a relative volatility of 1.3.

EXAMPLE 4

A solution comprising 270 grams of trichloroethylene and 30 grams of isobutanol was placed in the stillpot of the 7.3 theoretical plate rectification column. When refluxing began, an extractive agent comprising n-octanol was pumped into the column at a rate of 15 ml/min. The temperature of the extractive agent as it entered the column was 85° C. After establishing the feed rate of the extractive agent, the heat input to the trichloroethylene-isobutanol in the stillpot was adjusted to give a total reflux rate of 40 ml/min. After two hours of operation, the overhead and bottoms samples were collected and analysed. The overhead analysis was 97.7% trichloroethylene, 2.3% isobutanol and the bottoms analysis was 84.8% trichloroethylene, 15.2% isobutanol. This gives an average relative volatility of 1.31 for each theoretical plate. This data is presented in Table 6.

EXAMPLE 5

Seventy grams of the trichloroethylene-2-butanol azeotrope and 30 grams of 2-methyl-1-pentanol were charged to the vapor-liquid equilibrium still and refluxed for two hours. Analysis indicated a vapor composition of 88.1% trichloroethylene, 11.9% 2-butanol; a liquid composition of 80.5% trichloroethylene, 19.5% 2-butanol which is a relative volatility of 1.75.

EXAMPLE 6

A solution comprising 250 grams of trichloroethylene and 50 grams of 2-butanol was placed in the stillpot of the 7.3 theoretical plate glass perforated plate rectification column. When refluxing began, an extractive agent comprising 2-methyl-1-pentanol was pumped into the column at a rate of 15 ml/min. The temperature of the extractive agent as it entered the column was 85° C. After establishing the feed rate of the extractive agent, the heat input to the trichloroethylene-2-butanol in the stillpot was adjusted to give a total reflux rate of 40 ml/min. After two hours of operation, the overhead and bottoms samples were collected and analysed. The overhead analysis was 98.2% trichloroethylene, 1.8% 2-butanol and the bottoms analysis was 65.6% trichloroethylene, 34.4% 2-butanol. This gives an average relative volatility of 1.59 for each theoretical plate. This data is presented in Table 9.

EXAMPLE 7

Seventy grams of the t-butanol-trichloroethylene azeotrope and 30 grams of n-butyl acetate were charged to the vapor-liquid equilibrium still and refluxed for fourteen hours. Analysis indicated a vapor composition of 55.5% t-butanol, 44.5% trichloroethylene; a liquid composition of 31.7% t-butanol, 68.3% trichloroethylene which is a relative volatility of t-butanol to trichloroethylene of 1.7.

EXAMPLE 8

A solution comprising 170 grams of trichloroethylene and 30 grams of t-butanol was placed in the stillpot of the 7.3 theoretical plate glass perforated plate rectification column. When refluxing began, an extractive agent comprising n-butyl acetate was pumped into the column at a rate of 15 ml/min. The temperature of the extractive agent as it entered the column was 85° C. After establishing the feed rate of the extractive agent, the heat input to the trichloroethylene-t-butanol in the stillpot was adjusted to give a total reflux rate of 40 ml/min. After two hours of operation, the overhead and bottoms samples were collected and analysed. The overhead analysis was 92.2% t-butanol, 7.8% trichloroethylene and the bottoms analysis was 4.1% t-butanol, 95.9% trichloroethylene. This gives an average relative volatility of t-butanol to trichloroethylene of 2.15 for each theoretical plate. This data is presented in Table 12.

I claim:

1. A method for recovering trichloroethylene from a mixture of trichloroethylene and n-butanol which comprises distilling a mixture of trichloroethylene and n-butanol in the presence of about one part of an extractive agent per part of trichloroethylene-n-butanol mixture, recovering the trichloroethylene as overhead product and obtaining the n-butanol and the extractive agent from the stillpot, wherein said extractive agent consists of one material selected from the group consisting of n-decanol, n-nonyl alcohol, n-octanol, n-hexyl alcohol, tetrahydrofurfuryl alcohol, isodecyl alcohol, diisobutyl carbinol, methyl amyl alcohol, cyclohexanol, phenethyl alcohol, benzyl alcohol, 2-methyl pentanol, methyl isobutyl carbinol, isophorone, 5-methyl-2-hexanone, diisobutyl ketone, 2-heptanone, 3-octanone, 2,6-dimethyl-4-heptanone, acetonylacetone, 2-octanone, ethyl valerate, ethyl isovalerate, isobutyl isobutyrate, isobornyl acetate, 1-methoxy-2-propanol acetate, dimethylsulfoxide, dimethylformamide, dimethylacetamide, acetophenone and sulfolane.

2. A method for recovering trichloroethylene from a mixture of trichloroethylene and isobutanol which comprises distilling a mixture of trichloroethylene and isobutanol in the presence of about one part of an extractive agent per part of trichloroethylene-isobutanol mixture, recovering the trichloroethylene as overhead product and obtaining the isobutanol and the extractive agents from the stillpot, wherein said extractive agent consists of one material selected from the group consisting of benzyl alcohol, 2-methyl-1-pentanol, isohexyl alcohol, 4-methyl-2-pentanol, tetrahydrofurfuryl alcohol, cyclohexanol, n-octanol, 2-octanol, isooctanol, 2-ethyl-1-hexanol, diisobutyl carbinol, heptyl alcohol, phenethyl alcohol, diacetone alcohol, isoamyl alcohol, nonyl alcohol, n-decanol and isophorone.

3. A method for recovering trichloroethylene from a mixture of trichloroethylene and 2-butanol which comprises distilling a mixture of trichloroethylene and 2-butanol in the presence of about one part of an extractive agent per part of trichloroethylene-2-butanol mixture, recovering the trichloroethylene as overhead product and obtaining the 2-butanol and the extractive agent from the stillpot, wherein said extractive agent consists of one material selected from the group consisting of isoamyl alcohol, hexyl alcohol, diacetone alcohol 2-ethyl butanol, 4-methyl-2-pentanol, diisobutyl carbinol, benzyl alcohol, tetrahydrofurfuryl alcohol, 3-methyl-1-butanol, 1-octanol, 2-methyl-1-pentanol, 3-phenyl-1-propanol, isooctyl alcohol, heptyl alcohol, 3-methyl-3-pentanol, cyclohexanol, 2-ethyl-1-hexanol and isononyl alcohol.

4. A method for recovering t-butanol from a mixture of t-butanol and trichloroethylene which comprises distilling a mixture of t-butanol and trichloroethylene in the presence of about one part of t-butanol trichloroethylene mixture, recovering the t-butanol as overhead product and obtaining the trichloroethylene and the extractive agent from the stillpot, wherein said extractive agent consists of one material selected from the group consisting of n-butyl acetate, n-amyl acetate, n-propyl acetate, isobutyl acetate, hexyl acetate, 2-pentanone, 3-pentanone, 5-methyl-2-hexanone, methyl isobutyl ketone, methyl isopropyl ketone, 3-heptanone, methyl isoamyl ketone, 2-methoxyethyl ether acetate, 1-methoxy-2-propanol acetate, 3-hexanone, diisobutyl ketone, ethyl propionate, 4-methyl-2-pentanone, isoamyl acetate, ethyl isovalerate, ethyl butyrate, 1-methoxy-2-propanol, ethyl valerate, 3-ethoxy propionate 2,4-pentanedione, isobutyl butyrate, ethyl ethoxy propionate and isobutyl isobutyrate.

* * * * *